US00PP15453P2

(12) United States Plant Patent
Olesen et al.

(10) Patent No.: US PP15,453 P2
(45) Date of Patent: Dec. 21, 2004

(54) ROSE PLANT NAMED 'POULHT003'

(50) Latin Name: *Rosa hybrid*
Varietal Denomination: POULht003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,739

(22) Filed: Mar. 29, 2004

(51) Int. Cl.[7] ..... A01H 5/00
(52) U.S. Cl. ..... Plt./135
(58) Field of Search ..... Plt./135

*Primary Examiner*—Anne Marie Grunberg
*Assistant Examiner*—Annette H Para

(57) ABSTRACT

A new garden rose plant of the hybrid tea class which has abundant, apricot flowers and attractive foliage. This new and distinct variety has shown to be uniform and stable in the resulting generations from asexual propagation.

3 Drawing Sheets

Botanical classification: *Rosa hybrid.*
Variety denomination: 'POULht003'.

SUMMARY OF THE INVENTION

The present invention constitutes a new and distinct variety of garden rose plant which originated from a controlled crossing between the female parent, an un-named seedling, and the male parent 'POULduce', described and illustrated in U.S. Plant patent application Ser. No. 09/277,239 (abandoned) dated Mar. 26, 1999. The two parents were crossed during the summer of 1994 and the resulting seeds were planted in a controlled environment in Fredensborg, Denmark. The new variety is named 'POULht003'.

The new variety may be distinguished from its female seed parent by the following combination of characteristics:

1. While the seed parent has deep floral orange hues, flowers of 'POULht003' are lighter, orange-yellow in color.
2. 'Poulht003' is more disease resistant than the seed parent.
3. Flowers of the new variety, 'POULht003', have improved color retention than flowers of the seed parent.

The new variety may be distinguished from its pollen parent, 'POULduce' by the following combination of characteristics:

1. While flowers of the male pollen parent have a general tonality of Yellow Group 3C-4D, flowers of 'POULht002' have a general tonality of Yellow-Orange Group 19C.
2. While the male pollen parent has a flower petal count of 50–65 petals, 'POULht003' has 40 petals.

The objective of the hybridization of this rose variety was to create a new and distinct variety for garden use with unique qualities, such as:

1. Uniform and abundant apricot flowers with good color retention;
2. Vigorous, compact growth;
3. Disease resistance;
4. Classic rose flower form.

This combination of qualities is not present in previously available commercial cultivars of this type, known to the inventors, and distinguish 'POULht003' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark.

'POULht003' was selected in the spring 1995 by the inventors as a single plant from the progeny of the aforementioned hybridization.

Asexual reproduction of 'POULht003' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULht003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULht003'. Specifically illustrated in FIG. 1:

FIG. 1.2; Flower bud;

Figure 2:
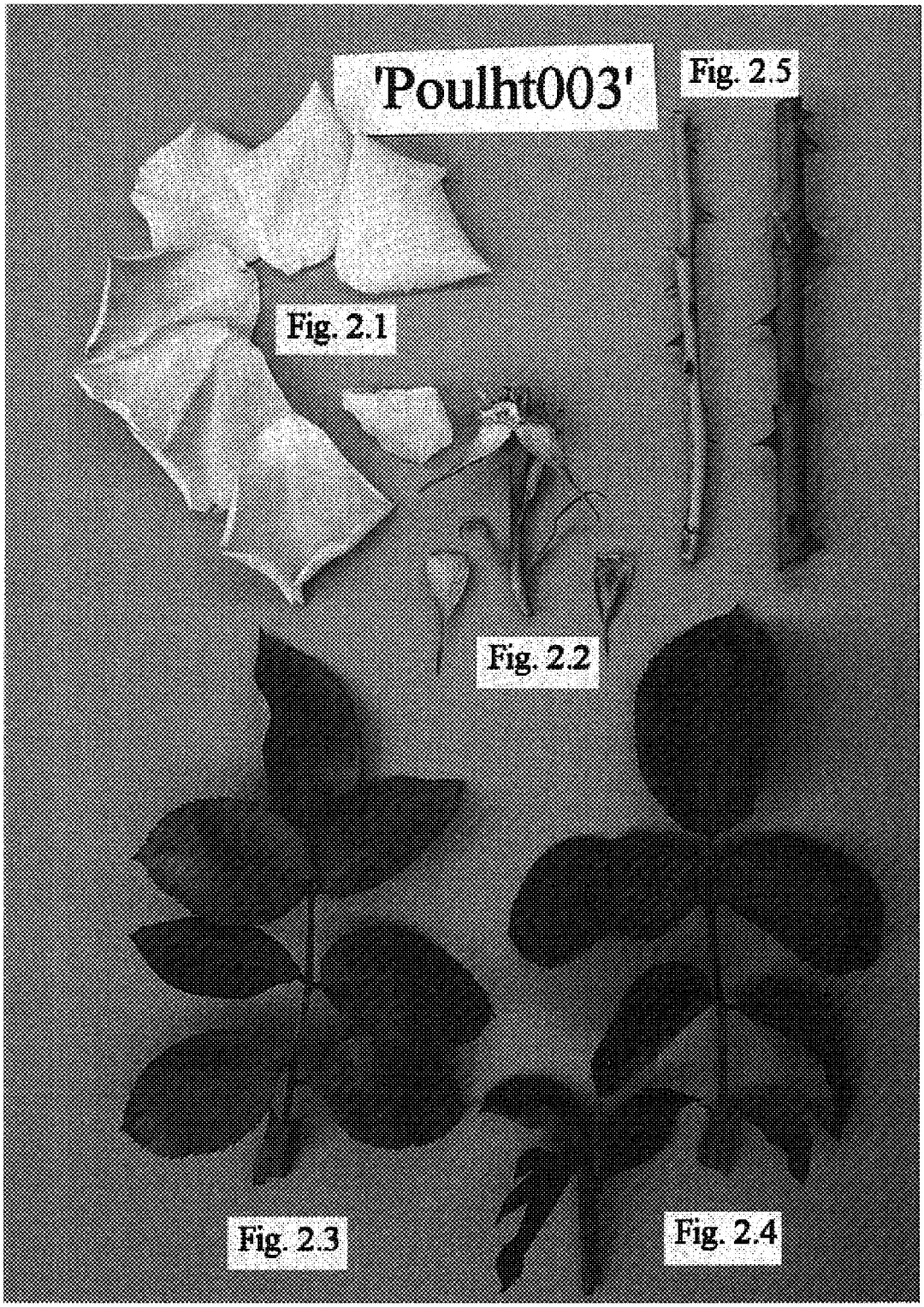

Specifically illustrated in FIG. 2:

FIG. 2.1; Flower petals, detached;

FIG. 2.2; Sepals, receptacle, and peduncle;

FIG. 2.3; Mature leaf;

FIG. 2.4; Juvenile leaves exhibiting anthocyanin;

FIG. 2.5; Mature and juvenile stems exhibiting thorns.

Figure 3:
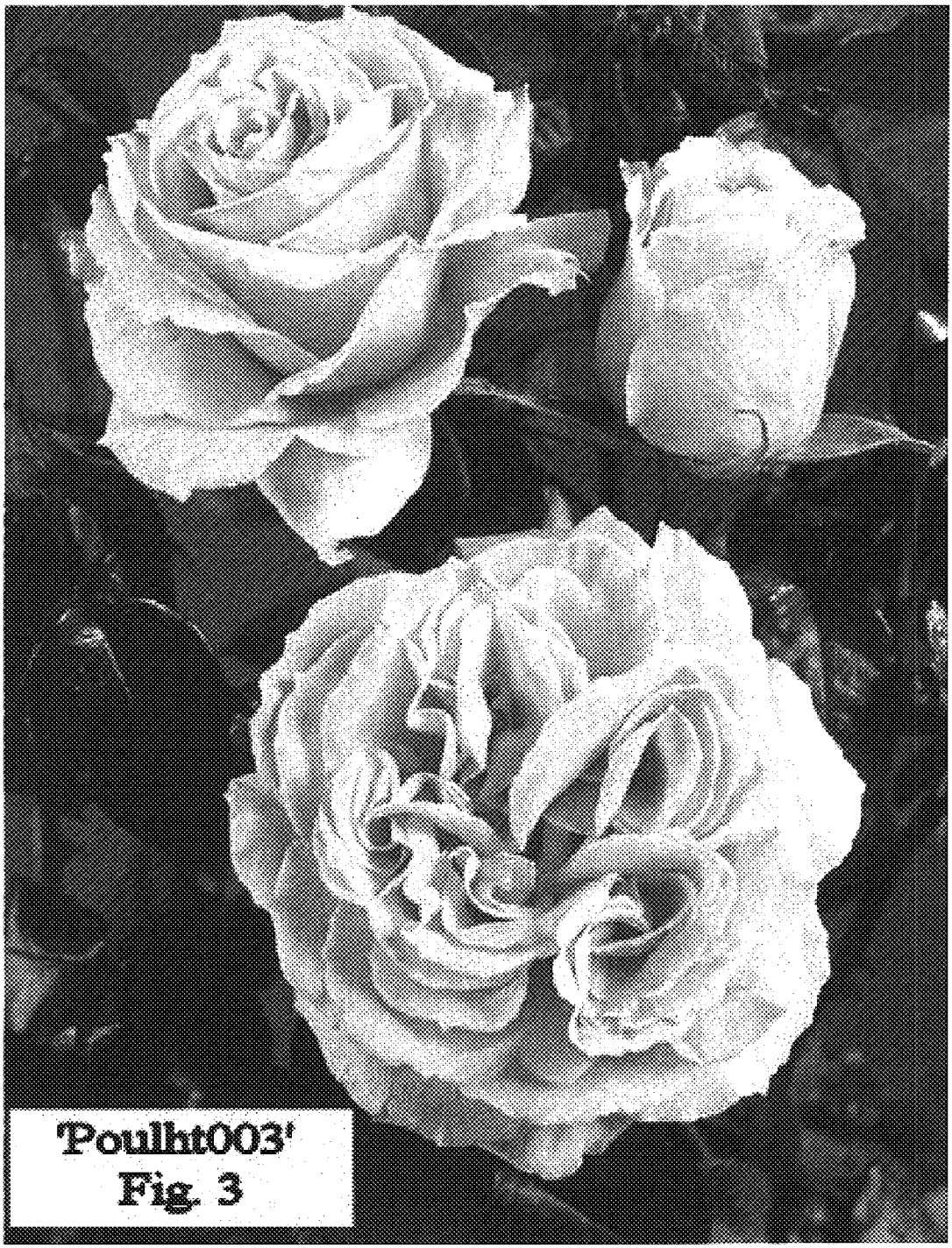

Specifically illustrated in FIG. 3:

FIG. 3; Open flowers.

DETAILED DESCRIPTION OF THE VARIETY

The following is a description of 'POULht003', as observed in its growth in a field nursery in Jackson County, Oreg. Observed plants are 3 years of age and were grown on *Rosa multiflora* rootstock. Color references are made using The Royal Horticultural Society (London, England) Colour Chart, 1995, except where common terms of color are used.

For a comparison, several physical characteristics of the rose variety 'JACfehon', a rose variety described and illustrated in U.S. Plant Pat. No. 11,617 issued Nov. 7, 2000, are compared to 'POULht003' in Chart 1.

CHART 1

| Petalage | 'Poulht003' 40 petals | 'JACfehon' 30 to 35 petals |
|---|---|---|
| Petal color: upper surface of outer petals | Yellow-Orange Group 19C with intonations of Yellow Group 7D at basal zone. | Yellow-Orange Group 19C |
| Color of flower petals as sepals divide. | Orange Group 28C. | Yellow-Green Group 154C at base. Yellow-Orange Group 22C towards the tip. |

FLOWER AND FLOWER BUD

Blooming habit: Recurrent.

Flower bud:

*Size.*—40 mm in length frombase of receptacle to the tip of the bud. Bud diameter is 20 mm.

*Bud form.*—Long and pointed ovoid, broadening at the base.

*Bud color.*—As sepals unfold, petals are Orange Group 28C. At ¼ opening petals are Yellow Group 4B with intonations of Red Group 42B.

*Sepals.*—Upper Surface: Color: Yellow-Green Group 145B with very weak anthocyanin Greyed-Red Group 182A. Surface: Strongly pubescent. Lower Surface: Color: Yellow-Green Group 145A. Anthocyanic pigments the color of Greyed-Red Group 182A. Sepal Shape: Sepal apex is cirrhose. Base is flat at union with receptacle. Sepal Margin: Margins have medium foliaceous appendages on three of the five sepals. Stipitate glands present in medium quantity. Size: 40 mm (l)×15 mm (w).

*Receptacle.*—Surface: Smooth and glabrous. Shape: Urn-shaped. Size: 10 mm (h)×10 mm (w). Color: Yellow-Green Group 145A. Anthocyanic pigments the color of Greyed-Red Group 181C observed.

*Peduncle.*—Surface: Somewhat rough. Stipitate glands are very fragrant. Length: 30 to 35 mm. Color: Yellow-Green Group 145C. Anthocyanic pigments the color of Greyed-Red Group 181C. Strength: Strong.

*Borne.*—In clusters of 1 to 4 flower buds per stem.

Flower bloom:

*Fragrance.*—Light floral scent.

*Duration.*—The blooms have a duration on the plant of approximately 7 to 10 days. Petals fall cleanly away from plant after flowers have fully matured.

*Size.*—Flower diameter is 115 mm when open. Flower depth is 60 m.

*Form.*—Classic hybrid tea shape with a tight center. Shape of flower when viewed from the side: Upon opening, upper part:Flat. Upon opening, lower part-:Flattened convex. Open flower, upper part: Flat. Open flower, lower part: Convex.

Petalage: On average 40 petals under normal conditions with 10 petaloids.

Color: Upon opening, petals:

*Outermost petals.*—Outer side: Yellow-Orange Group 19C with strong intonations of Red Group 38B. Inner Side: Yellow-Orange Group 19C with intonations of Yellow Group 7D at basal zone.

*Innermost petals.*—Outer side: Yellow-Orange Group 19C with strong intonations of Red Group 38B. Inner Side: Yellow-Orange Group 19C with intonations of Yellow Group 7D at basal zone.

Upon opening, basal petal spots:

*Outermost petals.*—Outer side: Yellow Group 5D. Inner Side: Yellow Group 5C to 5B.

*Innermost petals.*—Outer side: Yellow Group 5D. Inner Side: Yellow Group 5C to 5B.

After opening, petals:

*Outermost petals.*—Outer side: Yellow-Orange Group 19C with strong intonations of Red Group 38B. Inner Side: Yellow-Orange Group 19C with intonations of Yellow Group 7D at basal zone.

*Innermost petals.*—Outer side: Yellow-Orange Group 19C with strong intonations of Red Group 38B. Inner Side: Yellow-Orange Group 19C with intonations of Yellow Group 7D at basal zone.

After opening, basal petal spots:

*Outermost petals.*—Outer side: Yellow Group 5D. Inner Side: Yellow Group 5C to 5B.

*Innermost petals.*—Outer side: Yellow Group 5D. Inner Side: Yellow Group 5C to 5B.

General tonality: On open flower Yellow-Orange Group 19C. No change in the general tonality at the end of the $7^{th}$ day.

Petals:

*Petal reflex.*—Strongly.

*Margin.*—Entire and uniform. Very weak undulations of margin observed.

*Shape.*—Apex is slightly pointed to round. Base shape is rounded.

*Size.*—50 to 55 mm (l)×50 mm (w).

*Texture.*—Smooth.

*Thickness.*—Thick.

*Arrangement.*—Not Formal.

Petaloids:

*Quantity.*—8 to 10.

*Color.*—Orange Group 24C, Yellow Group 5A and Red Group 38B.

*Size.*—34 mm (l)×25 mm (w).

*Shape.*—Acute base. Round apex.

Reproductive organs:

*Pistils.*—Length: 5 mm. Quantity: 65 (actual count).

*Pollen.*—None observed.

*Anthers.*—Size: 3 mm long. Color: Yellow-Orange Group 14B. Quantity: 90 (actual count).

*Filaments.*—Color: Yellow-Orange Group 15B. Length: 9 to 14 mm.

*Stigmas.*—Inferior relative to the length of the filaments and to the height of the anthers. Color: Yellow-Orange Group 18C.

*Styles.*—Color: Orange-Red Group 34A to Orange-Red Group 33B.

*Hips.*—None observed in the field nursery in Jackson County Oreg.

PLANT

Plant growth: Moderate, upright to bushy. When grown as a budded field grown plant on *Rosa multiflora* understock, the average height of the plant is 100 to 150 cm and the average width is 100 cm.

Stems:

*Color*.—Young wood: Yellow-Green Group 145A to 145B with anthocyanic intonations of Greyed-Red Group 181B. Older wood: Yellow-Green Group 144C.

*Surface texture*.—Young wood: Smooth. Older wood: Smooth.

Thorns:

*Incidence*.—10 thorns per 10 cm of stem.

*Size*.—Average length: 9 mm.

*Color*.—Greyed-Red Group 181A to 182A.

*Shape*.—Deeply concave to concave.

Plant foliage: Normal number of leaflets on normal leaves in middle of the stem: 7 leaflets.

*Compound leaf size*.—185 mm (l)×125 mm (w).

*Quantity*.—Average to very.

*Color*.—Mature Foliage: Upper surface: Green Group 137B. Lower surface: Green Group 138C. Juvenile foliage: Upper surface: Greyed-Purple Group 183A to 187A. Lower surface: Greyed-Purple Group 183A to 187A. Anthocyanin: Location: Juvenile foliage and new shoots. Color: Greyed-Purple Group 183C.

Plant leaves and leaflets:

*Stipules*.—Size: 25 to 30 mm in length. Shape: Linear with outward extending apecies. Quantity: 2 per compound leaf. Margins: Finely serrated with abundant stipitate glands. Color: Yellow-Green Group 144B to 144C. Anthocyanin observed at margins, Greyed-Purple Group 183C.

*Petiole*.—Length: 45 to 50 mm. Above: Color: Yellow-Green Group 144B. Anthocyanin the color of Greyed-Purple Group 185B. Underneath: Very fragrant stipitate glands present. Lightly pubescent margins.

*Rachis*.—Length: 45 to 50 mm. Above: Color: Yellow-Green Group 144B. Anthocyanin: Greyed-Purple Group 185B. Underneath: Very fragrant stipitate glands present with light pubescence.

*Leaflet*.—Edge: Serrated. Size: 42 to 65 m (l)×36 to 46 mm (w). Shape: Generally ovate. Leaflet base is rounded. Apex shape is Mucronate. Texture: Smooth. Thickness: Thin. Arrangement: Odd pinnate. Venation: Reticulate. Glossiness: Moderately glossy.

Disease resistance: Above average resistance to mildew, rust, black spot, and *Botrytis* under normal growing conditions in Jackson County, Oreg.

Cold hardiness: The variety 'POULht003' has been found to be cold tolerant to USDA Cold Hardiness Zone 6.

It is claimed:

1. A new and distinct variety of rose plant of the hybrid tea rose class named 'POULht003', substantially as herein illustrated and described as a distinct and novel rose variety due to its abundant apricot flowers, disease resistance, and extended period of bloom.

* * * * *

Figure 1:
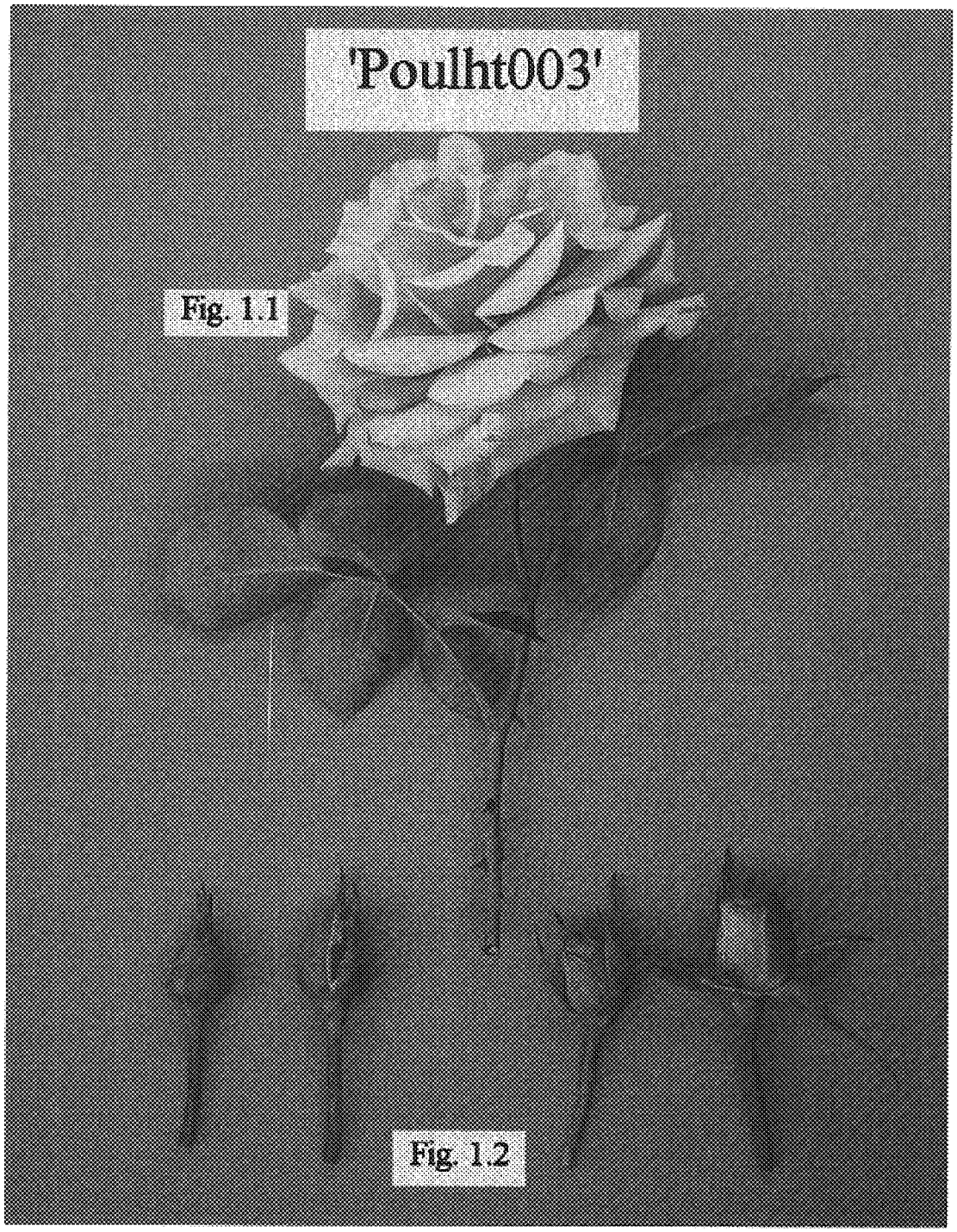
FIG. 1.1; Stem showing open flower and the attachment of leaves, buds, and peduncles.

'Poulht003'
Fig. 1.1
Fig. 1.2

'Poulht003'
Fig. 2.5
Fig. 2.1
Fig. 2.2
Fig. 2.3
Fig. 2.4

'Poulht003'